(12) United States Patent
Tereschouk

(10) Patent No.: US 7,419,321 B2
(45) Date of Patent: Sep. 2, 2008

(54) HAND APPLICATOR OF ENCAPSULATED LIQUIDS

(76) Inventor: Misha Tereschouk, P.O. Box 223, St. Petersburg (RU) 195279

( * ) Notice: Subject to any disclaimer, the term of this patent is extended or adjusted under 35 U.S.C. 154(b) by 60 days.

(21) Appl. No.: 11/123,133

(22) Filed: May 6, 2005

(65) Prior Publication Data

US 2006/0147250 A1      Jul. 6, 2006

Related U.S. Application Data

(60) Provisional application No. 60/641,268, filed on Jan. 5, 2005.

(51) Int. Cl.
*B43K 5/14*      (2006.01)
(52) U.S. Cl. ................ 401/133; 401/132; 401/201; 401/198
(58) Field of Classification Search ................ 401/132, 401/133, 199, 196, 198, 201, 1
See application file for complete search history.

(56) References Cited

U.S. PATENT DOCUMENTS

| | | | | |
|---|---|---|---|---|
| 2,209,914 A | * | 7/1940 | Wiesendanger, Jr. et al. | 401/132 |
| 4,291,697 A | * | 9/1981 | Georgevich | 401/132 |
| 4,596,481 A | * | 6/1986 | Tanaka | 401/132 |
| 4,665,901 A | * | 5/1987 | Spector | 401/8 |
| 4,674,237 A | * | 6/1987 | Sullivan | 451/523 |
| 5,090,832 A | * | 2/1992 | Rivera et al. | 401/132 |
| 5,126,070 A | * | 6/1992 | Leifheit et al. | 252/186.36 |
| 5,704,723 A | * | 1/1998 | Salisian | 401/8 |
| 6,167,890 B1 | * | 1/2001 | Gueret | 132/200 |
| 6,508,604 B1 | * | 1/2003 | Bechmann et al. | 401/132 |
| 2003/0077106 A1 | * | 4/2003 | Weihrauch | 401/196 |
| 2004/0258457 A1 | * | 12/2004 | Legendre | 401/133 |

* cited by examiner

*Primary Examiner*—Khoa D Huynh

(57) ABSTRACT

A hand applicator of encapsulated liquids, such as cosmetic, hygienic, and pharmaceutical formulations or household chemicals, of different viscosity. When the user squeezes the applicator in her hand, the capsule inside it ruptures, possibly with a clap, and releases a liquid that after being collected by the drain passes through the perforated dissector to get evenly distributed in the absorber and then evenly applied on skin or other surfaces. Inert and impermeable capsules ensure stability of stored liquid formulations. Pressurized capsules are easily tactilely located and crashed. A capsule may be permanently or elastically fixed within the applicator. The applicator may include several capsules that may contain different liquids. A refillable applicator can be refilled with new capsules and used more than once. A transparent impermeable back side the applicator enhances hygiene and creates visibility of the capsule. An impervious glove-applicator for applying hazardous substances is disclosed.

17 Claims, 5 Drawing Sheets

HAND APPLICATOR OF ENCAPSULATED LIQUIDS

This application claims the benefit of U.S. Provisional Application No. 60/641,268 filed Jan. 5, 2005.

BACKGROUND OF THE INVENTION

1. Field of the Invention

The invention relates to cosmetics, personal care products, and external use pharmaceuticals, and more particularly to topical applicators of encapsulated liquids used for cosmetic, hygienic, or medical purposes.

2. Description of the Prior Art

It is known that liquid cosmetic, hygienic, and external use pharmaceutical formulations can be manufactured in hermetically sealed single-use capsules that ensure a better stability over the storage period, than is allowed by reopened bottles, jars, and other sorts of containers or by packages of moisturized tissues and wipes. A single applicator containing both an absorber (usually, a sponge) and a capsule of a liquid that is crashed by the user in her hand before an application obviates the need of having a separate container of a liquid and an applicator for it.

U.S. patent application Ser. No. 10/198,055 (filed Jul. 19, 2002) describes a cosmetic applicator containing a bubble (of an unspecified material) of a cosmetic product, upon burst of which the product migrates through the body (polyurethane foam) of the applicator to its front (working) surface. A distinctive feature of the disclosed applicator is having a protective removable cover (polyethylene) over the front surface of the applicator.

The inventors propose a number of solutions to alleviate the problem of delivering a cosmetic product to the working surface of the applicator. First, the user should apply additional pressure to the backing layer of the applicator to force migration of the cosmetic product through the applicator body to the front surface. Second, the side of the bubble adjacent the rear surface of the applicator is made weaker than the opposite side of the bubble to ensure that the product is released on the side facing the rear surface to facilitate its migration through the applicator body to the front surface. Third, a cosmetic product is placed substantially centrally of the applicator. Fourth, the description of the manufacture process of applicators and bubbles might imply that a bubble can be fixed within the applicator.

U.S. patent application Ser. No. 09/986,264 (filed Nov. 8, 2001) discloses a cosmetic article (a wipe) comprising a substrate (a sponge) with which a dry cosmetic composition and breakable capsules (of an unspecified material) or microcapsules including a liquid (water) are associated. Upon breaking of the capsules, the liquid wets the cosmetic composition.

A major problem outlined in that application is that capsules are often hard to crash in hand. In order to inhibit movement of bigger capsules, the inventor suggests fixing them with positioning members or by an adhesive. The inventor also proposes a compressing device where pulling an article containing capsules between rolls or squeezing it in a special compartment ensures breakage of the capsules. The problem of an even distribution of a cosmetic composition in the substrate is solved by preliminarily applying the composition in an aqueous solution to the substrate followed by drying the substrate. When later the applicator is squeezed, multiple microcapsules of water dispersed in the substrate break and the released water reconstitutes the formulation.

Accordingly, the primary object of this invention is to create a practically operable hand applicator of encapsulated liquids of different consistencies that would guarantee breakage of a capsule from a regular manual effort and a quick delivery of the released liquid to the working surface of the applicator. Another important object is to ensure an even distribution of the liquid over the whole working side of the applicator and hence an even application of the liquid on skin or other surfaces. Other objects of this invention are:

provide with an applicator that allows dosing a formulation being applied;

enhance stability during storage of formulations contained in capsules;

make an applicator convenient in use, particularly in terms of easily locating a capsule by the user, having an indication of its successful breakage, and conveniently holding the applicator in hand;

make an applicator more hygienic in use;

devise a more economical way of applying encapsulated liquids; and depict applications of this invention beyond cosmetics, personal care, and medicine.

SUMMARY OF THE INVENTION

This invention puts forward a practically operable hand applicator of encapsulated liquid formulations of different consistencies (solutions, lotions, creams, balms, gels) used for cosmetic, hygienic, medical, or other purposes. The applicator enables rupture of a capsule from a regular manual effort, a quick delivery of the released liquid to and its even distribution on the working side of the applicator, and hence an even application of the formulation on skin or other surfaces.

It has been discovered by this invention that the performance of a hand applicator of an encapsulated liquid can be considerably improved if the applicator is provided with a capsule that ruptures when upon squeezing the applicator the pressure inside it rises sufficiently high to push the liquid to the working side of the applicator, and with a perforated dissector of the squirt resulting from an abrupt release of the liquid from a bursting capsule. The pressure at rupture of the capsule should be no less than 40 mm Hg (ordinarily in the range from 80 to 300 mm Hg).

The dissector is placed between the capsule and the absorber and has numerous evenly spaced perforations. The capsule is loosely encased in the applicator or in a separate dissector bag. As a result, upon rupture of the capsule, the dissector evenly dissects the strong squirt of the released liquid into multiple trickles or spray that are readily absorbed by the absorber and an even distribution of the liquid on the working side of the applicator is achieved. In a preferred embodiment, the dissector has perforations only on its side that is opposite the working side of the applicator and the total area of perforations is less than 10% of the area of the dissector.

To ensure the evenness of distribution of the released liquid over the working side of the applicator, the invention proposes placing a drain over the dissector on the side of the capsule. The drain lets the released liquid freely flow through its channels and reach all perforations in the dissector. In a preferred embodiment the drain and dissector are made as a single low density polyethylene (LDPE) element—drainable dissector—which includes blunt knobs (disks) spaced between perforations.

To avoid dislodgment of a capsule under the user's fingers, the capsule may be permanently fixed within the applicator (preferably to the dissector) or a dissector bag that encases a capsule may be fixed within the applicator. The elastic compression of the capsule between the dissector and the back side of the applicator that are sealed together along their edges can also adequately immobilize the capsule and additionally contribute to the positive pressure inside it.

In order to help the user to tactilely locate a capsule in the applicator and then crash it in her hand, this invention proposes usage of a pressurized capsule containing a liquid under a positive pressure. Such a tense pressurized capsule is easily felt by fingers and lowers the manual effort needed to crash it by the value of the positive pressure inside it. The constant positive pressure inside a capsule should be no less than 40 mm Hg (ordinarily in the range from 50 to 200 mm Hg).

In a preferred embodiment, a LDPE film of 10-15 microns is used to make normal pressure capsules (pressure at rupture of 150-225 mm Hg) and a LDPE film of 15-20 microns is used to make pressurized capsules (pressure at rupture of 225-300 mm Hg). A 10 micron thick high density polyethylene film or an 80-120 micron thick LDPE film is used for the dissector.

To enhance stability of liquid formulations, particularly of those held in pressurized capsules, this invention proposes coating capsules with a film that enhances their impermeability and extends storage period. Acetone-soluble film-forming polymers may be used for this purpose (in a preferred embodiment, a 5-20% solution of nitrocellulose is used).

It has been found that a clap occurring when a capsule ruptures may help the user to decide if her manual effort was sufficient to crash the capsule and if the applicator is ready for use. A clapping capsule contains, in addition to a liquid, air or inert gas of no less than 10% by volume.

The absorber (of polyurethane or polyester in the preferred embodiment) is capable of fully and quickly absorbing the liquid released through perforations in the dissector, promptly spreading the liquid around to neighboring sites within the absorber, and readily releasing the liquid to surfaces being treated.

In a preferred embodiment, the back side of the applicator is formed by a transparent impermeable membrane (an 80-120 micron thick LDPE film), through which the user can clearly see the capsule and press right over it to crash it. Besides, the membrane eliminates a contact of the user's hand with a liquid formulation.

The applicator may have a grip by which the user can hold it while rubbing the skin. In a preferred embodiment the flipper-like grip made of a duplication of the back side of the applicator can be brought to the working upright position only after the capsule lying underneath ruptures and flattens.

The applicator of this invention may contain more than one capsule, which makes possible dosing a formulation and applying different formulations from different capsules.

A refillable applicator has a fastener for its reopening that allows refilling the applicator with new capsules. A refill may be composed of a capsule alone or of a capsule encased in a perforated dissector and may have a string by which it is removed from the applicator after use.

An impervious glove-applicator has a capsule of a hazardous liquid placed between the outside palm surface of the glove and the absorber that lines the glove. When the user clenches her hand in the glove-applicator, the capsule ruptures and the liquid infuses the absorber. The glove-applicator preferably includes the disclosed perforated dissector.

DETAILED DESCRIPTION OF THE INVENTION

Figure 1:
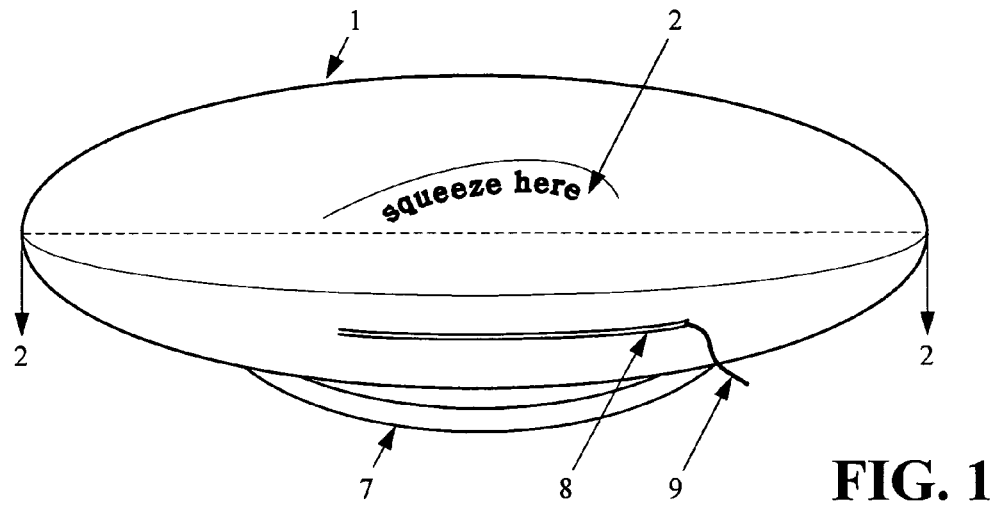
FIG. 1 is a front perspective view of the applicator of this invention.

This invention is a hand applicator of encapsulated liquid formulations of different consistencies used for cosmetic, hygienic, medical, or other purposes. The invention enables rupture of a capsule from a regular manual effort, a quick delivery of the released liquid to the working side of the applicator, an even distribution of the liquid over the whole working side area, and hence an even application of the formulation on skin or other surfaces.

The term "liquid" is used in this disclosure to denote a matter characterized by its readiness to flow, irrespective of the extent of fluidity, such as liquid, lotion, cream, or gel. The liquid may be composed of a single or multiple ingredients and be presented as solution or disperse system. The liquid may be makeup, makeup or varnish remover, toner, cleanser, surfactant, emulsifier, moisturizer, emollient, astringent, fragrance, antiperspirant, deodorant, tanning, sunscreen, antiseptic, antiinfective, antiinflammatory, anti-acne, vitamin, insect repellent, or another product. A "hand-breakable capsule" in this invention means a capsule that the user can crash in her hand by applying a normal manual effort.

Experiments with prior art applicators revealed difficulty locating and crashing a pliable capsule. Furthermore, the liquid from a crashed capsule did not evenly imbue the absorber of an applicator. Rather, the liquid amassed in the absorber near the rupture of the capsule and slowly migrated from there within a part of the absorber. Even after intensely rubbing the skin, the absorber might rest unevenly imbued leaving the skin without due treatment by the formulation and red as a result of dry rubbing. An excess of a thin liquid in the absorber close to the rupture site often caused its dripping out of the applicator. Thick liquids were harder to release from ruptured capsules and, though did not drip, built up near the rupture site to a bigger extent and infused the absorber even worse.

As overviewed in the background section above, the prior art recognizes the problems of hardly crashing capsules containing liquids and of an uneven distribution of liquids in applicators and proposes solutions for the former (fixation of capsules within an applicator; a compressing device for crashing capsules) and for the latter (applying an additional manual force to the back of the applicator; placing the capsule centrally; using a dry cosmetic composition and microcapsules of water dispersed in the applicator in advance). The present invention however solves these problems differently, by using capsule that ruptures when a high pressure inside it is reached, perforated dissector, drain, and transparent back side of the applicator. Additionally, this invention solves a not existing in the prior art problem of a disruptive hydraulic blow produced by the liquid released from a capsule that ruptures at a high pressure.

It has been discovered that the performance of a hand applicator of encapsulated liquids can be considerably improved if the applicator is provided with a capsule that ruptures at a high pressure that pushes the liquid being released to the absorber in the direction of the working side of the applicator. To be operable with usual consistencies of liquid cosmetic and pharmaceutical formulations, a capsule should rupture at a positive (i.e. exceeding the normal atmospheric pressure of 760 mm Hg) pressure of no less than 40 mm Hg (ordinarily, in the range from 80 to 300 mm Hg).

Further experiments showed that depending on the capsule material, the pressure inside a squeezed capsule causing it to rupture might be fairly high: about 300 mm Hg for a 20 micron thick low density polyethylene (LDPE) film and about 450 mm Hg for a 30 micron thick LDPE film. Upon rupture of such a capsule, a strong squirt of the liquid often streamed out in one direction and burst out through spongy walls of the applicator.

Therefore, in order to achieve an even distribution of the liquid over the whole area of the working side of the applicator and, respectively, an even application of the liquid on skin or other surfaces, a perforated dissector was devised that is able to dissect and disperse the squirt resulting from an abrupt release of the liquid from a breaking capsule. When a perforated dissector is used, the high pressure at rupture contributes to a faster and more even distribution of the liquid within the applicator.

Figure 2A:
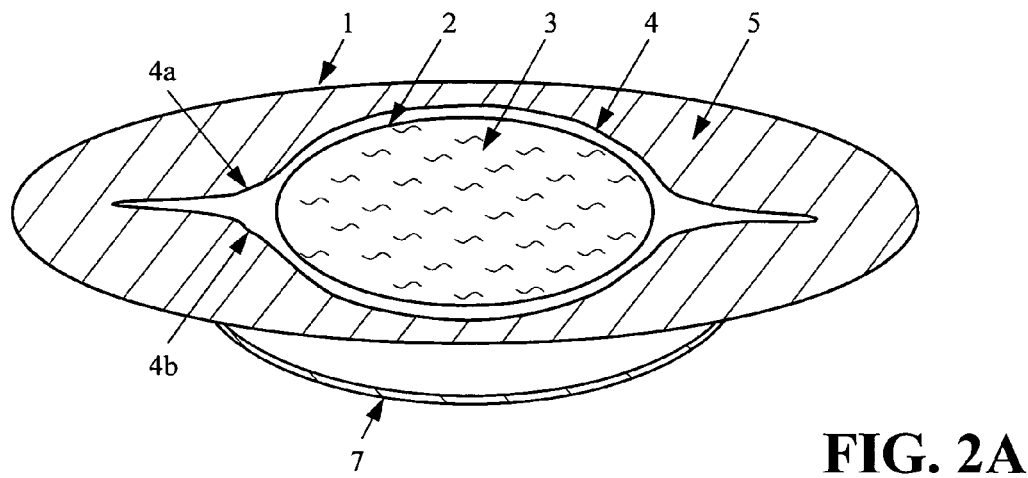
FIG. 2A is a front cross-sectional view of the applicator taken along line 2-2 in FIG. 1.
Figure 2B:
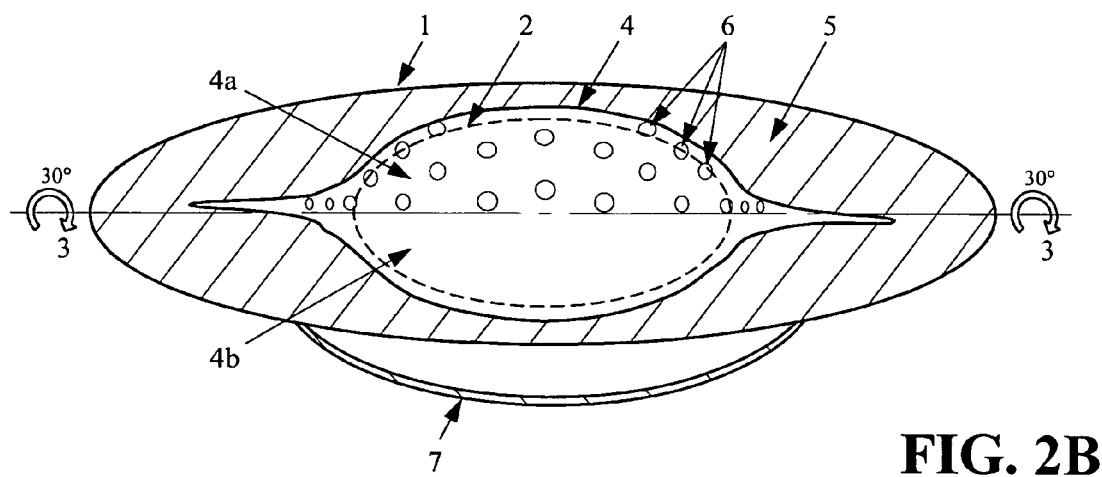
FIG. 2B is a front partial cross-sectional view of the applicator where its innermost part (the dissector with a capsule inside) remains uncut.
Figure 3:
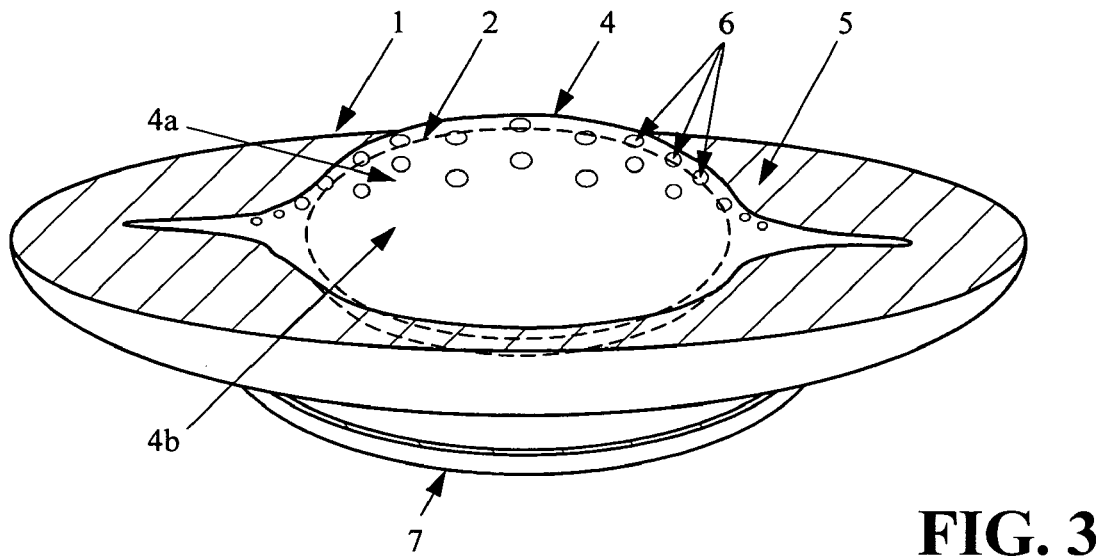
FIG. 3 is the result of rotation of the front partial cross-sectional view of the applicator shown in FIG. 2B by 30° backward around the frontal axis (the direction of rotation is indicated by circular arrows in FIG. 2B).

FIG. 1 is a front perspective view of an ellipsoid applicator according to this invention demonstrating a part of its working and, to a lesser extent, back sides. FIG. 2A is a front cross-sectional view of the applicator shown in FIG. 1 where the section is taken along line 2-2 in FIG. 1. FIG. 2B is a front partial cross-sectional view of the same applicator and differs from FIG. 2A in that its innermost part (the dissector with a capsule inside) remains uncut. FIG. 3 is the result of rotation of the front partial cross-sectional view of the applicator shown in FIG. 2B by 30° backward around the frontal axis (the direction of rotation is indicated by circular arrows).

Capsules of liquids may be hidden from the eye in the depth of a thick applicator. In order to ease visually locating a capsule in an applicator by the user, especially when a small capsule does not bulge, mark, sticker, or similar index of the location of the capsule in the applicator may be placed on its outer surface (see the SQUEEZE HERE sign in FIG. 1).

The depicted applicator has the working side that contacts a surface being treated and the back side that is in contact with the user's hand and to which a grip is usually attached. In FIG. 1, 2A, 2B the working side of the applicator is at top and the back side is at bottom. As these drawings illustrate, when the user squeezes the applicator 1 in her hand by pressing on the SQUEEZE HERE area corresponding to the location of the capsule 2, the capsule 2 gets compressed and ruptures releasing the liquid 3 it contains. The squirt of the released liquid 3 is evenly dissected by the perforated dissector 4 (composed of the perforated side 4a facing the working side of the applicator and the non-perforated back side 4b) in fine trickles and spray that are readily absorbed by the absorber 5. Then the liquid is evenly applied with the applicator on skin or other surfaces. (Perforations in the dissector 4 are shown as small circles 6.)

Since it is almost impossible to predict the location of a rupture in a capsule that has walls of uniform strength, the capsule 2 in this embodiment is wholly encased in the dissector 4.

Figure 4:
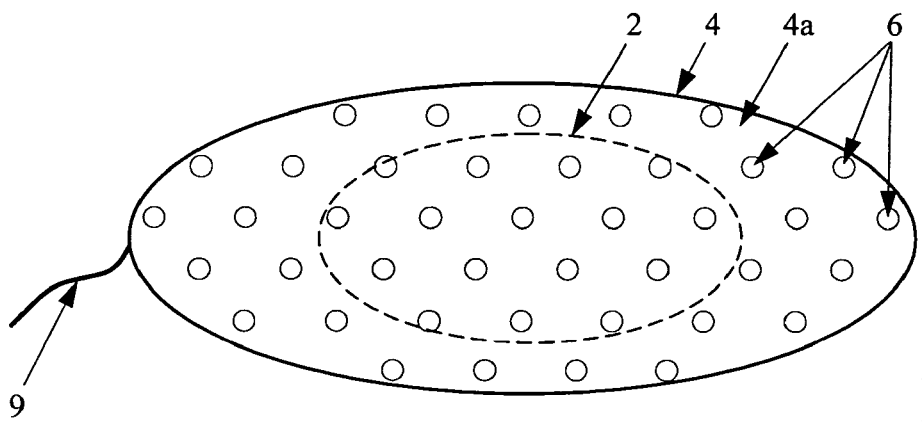
FIG. 4 is a top plan view of the dissector of this invention.
Figure 5:
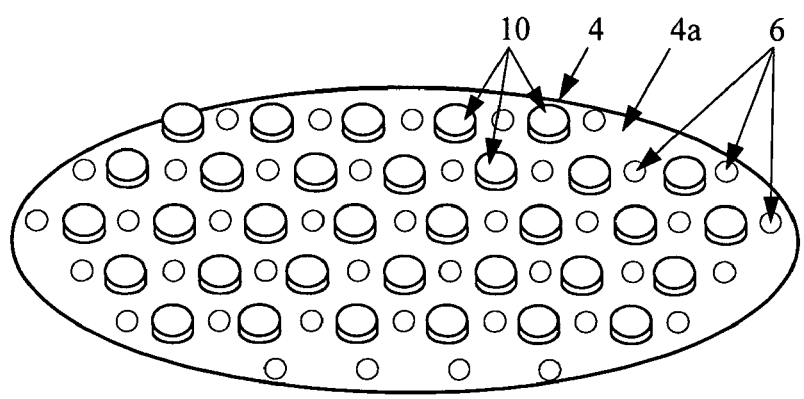
FIG. 5 is a top perspective view of the drainable dissector of this invention.

The capsule 2 being loosely (freely) encased in the dissector 4 (FIGS. 2A, 2B, 3) is important. This creates a space between a rupturing capsule and the dissector where an abruptly released liquid swiftly accumulates. As the liquid fills up this space, its pressure falls and equalizes throughout the space, and finally evenly dispersed and equally strong trickles run out of perforations in the dissector in the direction of the working surface of the applicator. Otherwise, when a dissector tightly embraces a capsule, there is no space between the capsule and the dissector for smoothing the hydraulic blow and therefore a strong squirt of the liquid from a ruptured capsule can break through the closest perforations in the dissector out of the applicator or can damage and tear the dissector. The minimum required volume of the enclosure formed by the dissector depends on the volume and viscosity of the liquid in a capsule, the number and size of perforations in the dissector, the compressing force and elasticity of the absorber (walls of the applicator), and the pressure at rupture of the capsule. For fluidic liquids (aqueous and alcohol solutions, thin lotions), given the capsule and dissector are made as described here in preferred embodiments, the volume of the dissector should be 1.5-2.5 times larger than the volume of the liquid in the capsule.

The dissector of this invention is made of a strong, flexible, thin, and non-absorbing material that can withstand the pressure of a squirt and that is also inert on contact with the liquid of the capsule. In a preferred embodiment the dissector is a bag of a ten-micron high density polyethylene (HDPE) film that loosely encases the capsule and its geometry generally repeats the shape of the inner cavity of the applicator (FIGS. 2A, 2B, 3).

The dissector of this invention has numerous evenly spaced perforations 6 (FIGS. 2B, 3, 4), owing to which it evenly dissects the strong squirt of the released liquid into multiple trickles or spray that can be readily and evenly absorbed by the absorber without an undue accumulation of the liquid near the rupture site. As a result, an almost even distribution of the liquid on the working side of the applicator is achieved.

Perforations may be of different shape, size, and area density. The size and density of perforations in the dissector depend on the consistency of the liquid and on the absorbability and porosity of the absorber. The less viscous the liquid is, the smaller and rarer perforations should be. For example, for an after-shave balm (viscosity of 0.2-1.0 Pa×s), two perforations per square centimeter, each of about ½-1 mm in diameter may be suitable while for an after-shave lotion (viscosity of 0.01-0.05 Pa×s), one perforation per square centimeter of about ¼-½ mm in diameter would do better. Normally, for a dissector to be operable with usual consistencies of liquid cosmetic and pharmaceutical formulations, the total area of perforations should be no more than 10% of the total area of the perforated side of the dissector. To achieve a better evenness of distribution of a liquid (particularly of a thick liquid) that may gather along the edge of an applicator, the dissector may have a non-uniform pattern of perforations where density of perforations decreases from the center to the edge.

FIG. 2B is a front cross-sectional view of the applicator 1 where the absorber 5 and grip 7 are shown cut while the dissector 4 with the capsule 2 inside remains uncut (the contour of the ovoid capsule 2 is shown by the dashed line). Evenly spaced perforations 6 are seen only on the side 4a of the dissector 4 overlooking the working side of the applicator while the back side 4b is not perforated. FIG. 3, which is the result of rotating the view of FIG. 2B backward by 30°, demonstrates more visibly the geometry of the dissector 4 having perforations 6 only on its side 4a. FIG. 4 is a top plan view of the dissector 4 showing its side 4a only, which has numerous evenly spaced perforations 6 and a contour of the capsule 2 lying underneath.

In a preferred embodiment, the dissector 4 has perforations only on its side 4a that is opposite the working side of the applicator and therefore directs the full strength of the dissected squirt toward that side thus contributing to a quick distribution of all released liquid over the working side. The other (non-perforated) side 4b may be provided by an impermeable membrane lining the back of the internal cavity of the applicator. Alternatively, a perforated dissector, rather than being a separate bag lying in the internal cavity of the applicator, may be composed of two plastic sheets forming the internal cavity of the applicator, one of which is perforated.

When the capsule and dissector are elastically fixed between resilient walls of the applicator, squeezing the applicator by the user, the rupture of the capsule, and the resulting squirt of the liquid normally do not cause a substantial dislocation of the capsule and dissector. In other situations (for example, when a capsule is too small relative to the size of a dissector or when a dissector does not have a uniform pattern of perforations), to avoid a dislodgment of the capsule and possibly dissector under the user's fingers, the capsule may be permanently fixed to the dissector or the dissector that encases the capsule may be fixed within the applicator or both. The fixation may be done by welding, bonding, stitching, or another suitable expedient. For example, a strip of the plastic sheet from which the capsule has been formed and that is left around the capsule can be welded to the adjacent part of the dissector.

Along with characteristics of the liquid and dissector and the geometrical relation between the capsule, dissector, and inner cavity of the applicator, a quick and complete release of the liquid from the ruptured capsule and dissector and an even distribution of the liquid within the absorber depend on the strength of the squirt abruptly released from the ruptured capsule. In its turn, the strength of the squirt depends on the pressure at which the capsule ruptures. Other parameters (capsule material; viscosity of the liquid) kept equal, the thicker the capsule, the stronger the head of a liquid upon its rupture.

However to crash in fingers a thick capsule producing a strong squirt could be hard. As noted above, this may require forcefully compressing the applicator to create a pressure of 300-450 mm Hg inside the capsule. To solve this problem and also to help the user tactilely locate a capsule in the applicator, this invention proposes usage of a pressurized capsule containing a liquid under a constant positive pressure: the higher the pressure inside a capsule, the lower the manual effort to crash it.

As a way of example, if a LDPE film of 20 microns is used to make a pliable capsule containing a liquid and the capsule ruptures at 300 mm Hg, the user may have difficulty locating the capsule and will have to apply a considerable manual force to squeeze a spongy applicator until the pressure inside the capsule rises from 0 to 300 mm Hg while in a situation where a capsule is made of the same material, but holds a liquid under 250 mm Hg, the same user would easily feel a hard tense capsule under the fingers and have to make only a mild effort to raise the pressure in the capsule by additional 50 mm Hg to crash it. The preferred value of the positive pressure inside a capsule depends on the material selected to make the capsule and should be high enough for the user to easily crash the capsule and at the same time low enough to prevent its inadvertent rupture during storage and handling.

To build an applicator with a pressurized capsule operable with usual consistencies of liquid cosmetic and pharmaceutical formulations using the described preferred materials, the constant positive (i.e., exceeding the normal barometric pressure) pressure inside the capsule should be set at no less than 40 mm Hg (ordinarily, in the range from 50 to 200 mm Hg).

It should be noted that while the use of the disclosed dissector is desirable for capsules that rupture at 40 mm Hg, the use of the dissector for thicker capsules with pressures at rupture of 80 mm Hg and higher, whether pressurized or not, is essential for a properly functioning applicator.

In order to ensure stability of liquid formulations during storage, capsules should be made of a material that is chemically inert and impervious for oxygen, water, and other chemicals present inside and outside the capsule. Generally, thickness of a material correlates with its impermeability. Besides, as discussed above, thicker capsules with a higher pressure at rupture generally provide with a better release and distribution of a liquid, which is particularly important for viscous liquids. Thicker films are also less prone to mechanical defects (scratches, tears, deformations with thinning) in manufacture and storage. Pressurized capsules can also be made of thicker materials. In any case, capsules should be thick enough to present an effective physical and chemical barrier for a stored liquid and, at the same time, be thin enough to be easily crashed in hand. As an additional requirement, a material for pressurized capsules should be somewhat elastic to facilitate the fill-and-seal procedure. In a preferred embodiment, a LDPE film of 10-15 microns is used to make normal pressure capsules (pressure at rupture of 150-225 mm Hg) and a LDPE film of 15-20 microns is used to make pressurized capsules (pressure at rupture of 225-300 mm Hg).

Figure 7:
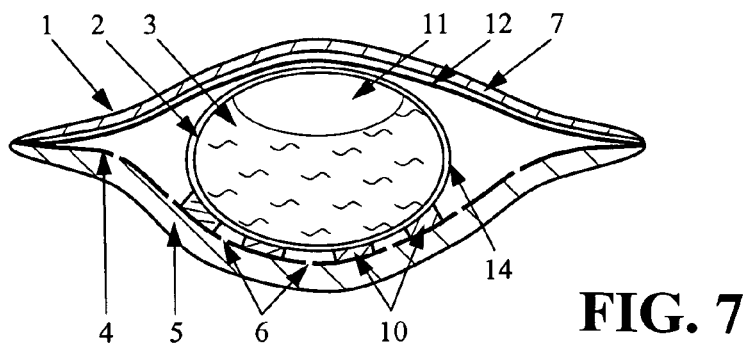
FIG. 7A is a front cross-sectional view of the applicator taken along line 7A-7A in FIG. 6A.
FIG. 7B is a front cross-sectional view of the applicator taken along line 7B-7B in FIG. 6A and FIG. 9.

To enhance stability of liquid formulations, particularly of those which are held in pressurized capsules, this invention proposes coating capsules with an inert material 14 that enhances their impermeability and extends storage period (FIG. 7). Such a material must be inert to the formulation and safe to humans in case it contacts the skin. Neither the coating material, nor its solvent being used shall penetrate the capsule. A coating must not dissolve in the liquid contained in a capsule when the capsule breaks. The thickness and elasticity of a coating should not affect much the ability of the capsule to rupture. Acetone-soluble film-forming polymers, such as cellulose esters, cellulose acetate and nitrocellulose, may be used for this purpose. A safe plasticizer may be added, given it does not worsen impermeability of the polymer. A film coating may be applied to a capsule by dipping, spraying, or in another way. In a preferred embodiment, a capsule containing a liquid is shortly dipped in 5-20% solution of nitrocellulose in acetone and then dried.

It has been found that when a capsule containing in addition to a liquid some gas (air or inert gas) ruptures, a clap occurs that may help the user to decide whether her manual effort was sufficient to crash the capsule and if the applicator is ready for use. An inert gas is more preferable in view of its inertness upon a prolonged contact with a liquid formulation. The gas content of a capsule should be no less than 10% by volume (under normal pressure) in order to produce a loud clap. In pressurized clapping capsules the volume of compressed gas may be less. Generally, the more gas a capsule contains and the higher the pressure at rupture is, the louder the clap is. As an example, clapping capsules of 2-3 ml contain nitrogen composing about half their volume (under normal barometric pressure).

The absorber of this invention should be capable of fully and quickly absorbing all of the liquid trickling through perforations in the dissector, promptly spreading the liquid around to neighboring sites within the absorber, and readily releasing the liquid to surfaces being treated when the applicator is gently compressed by the user. The ability of the absorber to fully absorb the liquid released from perforations in the dissector is determined primarily by its absorbability at rest and porosity.

In an absorbability test, a squeezed sample of an absorber is submerged in a liquid being used in the applicator. The sample then is released to let it get infused with the liquid, after which it is taken out of the liquid and the excess of the liquid is taken away or let flow down. The measured difference in the sample weight (or volume) before and after exposure to the liquid characterizes its absorbability at rest. Submerging a sample in a liquid mimics a situation when, thanks to the perforated dissector and drain (disclosed below), the absorber is evenly infused with a liquid. A selected absorber should be able to fully absorb all liquid released from perforations in the dissector. Otherwise, if absorbability is low, the excess of the liquid will leak out of the absorber, and if absorbability is too high, the absorber won't leave enough liquid during application onto a surface being treated.

The ability of an absorber to block the spray of a liquid coming out of perforations in the dissector is evaluated in a porosity test where a capsule is crashed with an effort deliberately somewhat exceeding the normal manual effort (for the sake of safety of the future applicator): if the spray bursts out through an absorber, the thickness of the absorber should be increased and the test rerun or, more preferably, another absorber with a similar absorbability at rest and yet less porosity should be tried. (Alternatively, a dissector with smaller perforations and/or a less viscous formulation may be tried.) While selecting a suitable absorber one should keep in mind an inverse relationship between its porosity and the time over which it fully absorbs a liquid. Other factors (viscosity; capillary attraction; density and size of perforations in a dissector; perforations outflow pressure) kept equal, the smaller and rarer pores are, the more time it will take to fully absorb a liquid.

The absorber used in this invention can be made of different types of sponges, fibers, or other absorbing materials that satisfy requirements of inertness to a liquid formulation, absorbability at rest, and porosity. An absorber may include a cover of velour or a similar fabric that makes its gliding over the skin smooth and pleasurable. In a preferred embodiment, a velour-covered 2 mm polyurethane foam sheet optionally reinforced by a thin loose polyamide mesh is used. A single material combining required absorbability and porosity with good softness (e.g. flocked polyurethane foam, fleece, thick velour) can be used as well (see description of a fleece absorber in a preferred embodiment below).

It should be noted that an even distribution of a liquid by the dissector allows a decrease in the thickness of an absorber and hence reduces the amount of the liquid the absorber finally retains after use. Both have positive economic implications.

To avoid a contact of the user's hand with a liquid formulation when using a prior art applicator would necessitate wearing an impermeable glove, particularly when a formulation is applied by someone else (nurse, caregiver, or cosmetician). The applicator of this invention has a grip by which the user can hold the applicator while applying the formulation on skin. A grip may be implemented in different ways (as handle, loop, fingerhold, and so on) and attached to the applicator by welding, bonding, stitching, or another suitable expedient. In the shown example, a grip is a silk ribbon 7 attached to the applicator 1, so that the user could pass her fingers between the ribbon and the back side of the applicator (FIGS. 1, 2A, 2B, 3) (see also the description of a flipper-like holder in a preferred embodiment below).

Depending on the purpose of use, the applicator may be of different shape and size. For example, an applicator of a cleanser for children's hands may have a shape of a small toy and contain a 2 ml capsule while an applicator implemented as a bathe sponge may be much thicker and contain a 5 ml capsule of shampoo.

The applicator of this invention may contain more than one capsule. This makes possible dosing and applying different formulations 3 from different capsules 2 (FIG. 8). Preferably capsules are permanently fixed within such an applicator and signs on its outer surface indicate which of the capsules contains what. As an example, capsules may be located in the corners of an applicator.

Dosing may be valuable when applying medications that are prescribed at different doses. The applied dose equals the contents of a capsule (or capsules) less the known residue retained by the absorber after a complete use.

Capsules containing liquids of different formulations (compositions) may be useful when a prolonged contact of ingredients of different formulations is undesirable in view of their interaction, or when a new substance should be formed extemporarily out of them, or when the user is to make a selection of a formulation. For example, a bathe sponge may contain separate capsules for shampoo and conditioner while a body care applicator may contain separate capsules of moisturizer and fragrance.

A refillable applicator presents a more economical way of applying encapsulated liquids. This applicator has a fastener 8 for its reopening that allows the user to refill the applicator with new capsules and thus use the applicator on more than one occasion FIGS. 1, 8. A refillable applicator also allows individually dosing formulations, i.e. applying cosmetic or pharmaceutical formulations in specified (prescribed) quantities as determined by the number and volume of capsules being used.

The fastener must be leak-proof for the liquid released from a capsule, inert on contact with it, and not interfering with its distribution in the applicator and application on skin. Such a fastener may be a zipper, an adhesive flap, a hook & eye, an opening narrowed by an elastic band, or a fastener with a linear elevation and a matching depression resiliently engaging each other, like the one used in Ziploc(™.) resealable plastic bags (FIGS. 1, 8). An adhesive flap is perhaps the cheapest fastener, however requires keeping contact surfaces of an opened flap clean to preserve adhesiveness on multiple use. In a preferred embodiment, a refillable applicator is implemented as a washable spongy pouch closed by a Ziploc (™)-like fastener 8 on the back side of the applicator (FIG. 1).

When necessary, the user removes the used capsule and dissector, washes the applicator, and inserts a refill (a new capsule encased in a new perforated dissector bag) into it. A refill may include a string 9 attached to the dissector 4, by which the used dissector with a ruptured capsule inside can be pulled out and easily removed from the applicator without contaminating the user's hands with the released liquid (FIGS. 1, 4). Attaching a string to the dissector may be done by welding, bonding, stitching, or another suitable expedient. FIG. 4 is a top plan view of a refill composed of capsule 2, dissector 4, and string 9. In another embodiment, a refill includes only a capsule while a non-removable dissector, the entrance of which is reopened by a fastener, remains in the applicator. In this case, a string is attached to the capsule.

Experiments with the disclosed applicator have revealed that some perforations in the dissector may get closed by the pressure of the user's fingers over the applicator or by the flat capsule itself that after rupture wets and often sticks to the dissector. Therefore the central area of the absorber corresponding to the location of the grip and capsule may stay insufficiently or unevenly imbued. To overcome this problem, the invention proposes a drain for draining the released liquid, i.e. for collecting the released liquid and its directing to all perforations in the dissector. The drain is placed over the dissector on the side of the capsule and creates over the dissector an incompressible space where the released liquid freely circulates. The drain may be implemented as rack, mesh, framework, support, or similar item of a not absorbing and not compressible material and allows the liquid freely flow through its channels or tunnels and access all perforations in the dissector. Alternatively a drain may be implemented as a system of sufficiently deep channels in the dissector at the bottom of which perforations are located.

Figure 6A:
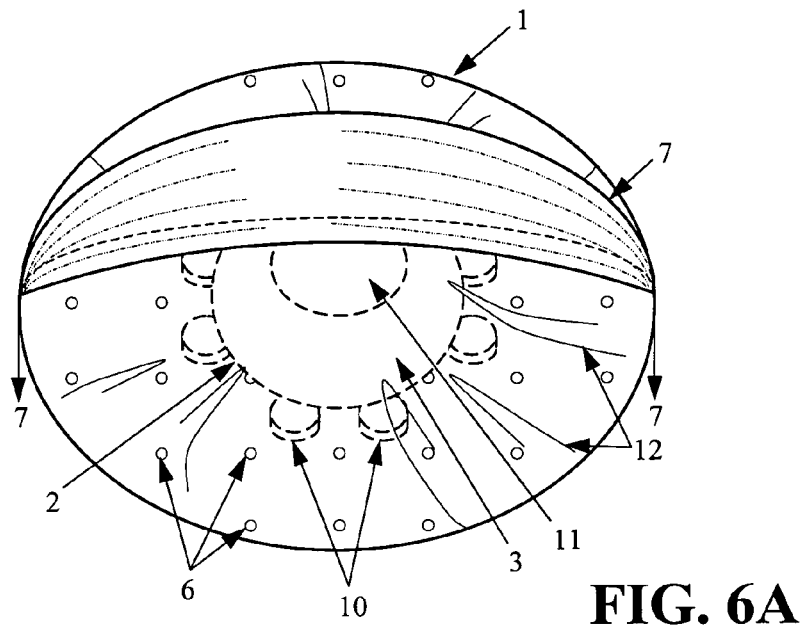
FIG. 6A is a top perspective view of the applicator of this invention in the storage state.
Figure 6B:
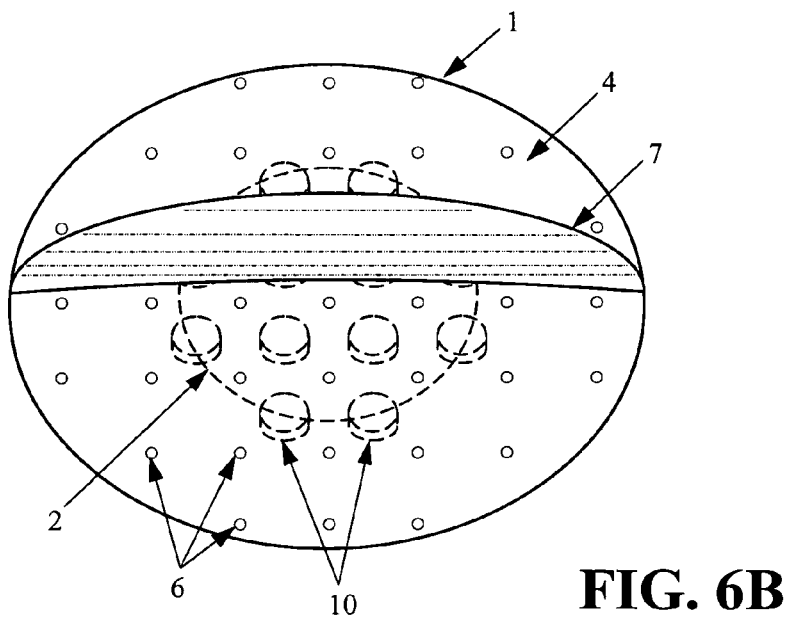
FIG. 6B is a top perspective view of the same applicator in the working state.

In a preferred embodiment the drain in the form of channels, is build of blunt knobs or disks 10 spaced between perforations 6 in the dissector 4 (FIGS. 5, 6A, 6B, 7A, 7B). Channels formed around knobs 10 over the dissector 4 on the side of the capsule 2 allow the released liquid freely flow to reach all perforations 6 in the dissector 4. After rupture, the flat capsule 2 lies on knobs 10 not contacting the dissector 4 and no longer closes perforations 6 in it (FIG. 6B). Likewise, the opposite membrane (the non-perforated back side 4b of the dissector of the applicator shown in FIGS. 2A, 2B, 3 or the back side 12 of the applicator shown in FIGS. 6A, 7A, 7B) does not get in contact with the perforated dissector and hence does not close its perforations either.

The drain and dissector in the preferred embodiment are made as a single element—drainable dissector—which prevents the drain shifting relative to the dissector during application and inadvertently blocking some perforations by the drain. Having one element instead of two is cost-saving as well. When a thermoplastic material, such as LDPE, is used, a drainable dissector can be manufactured by molding or by welding knobs to a dissector. The number, size, and density of knobs may be different and depend on characteristics of perforations, capsule, liquid, back side of the applicator, and grip.

Figure 7A:
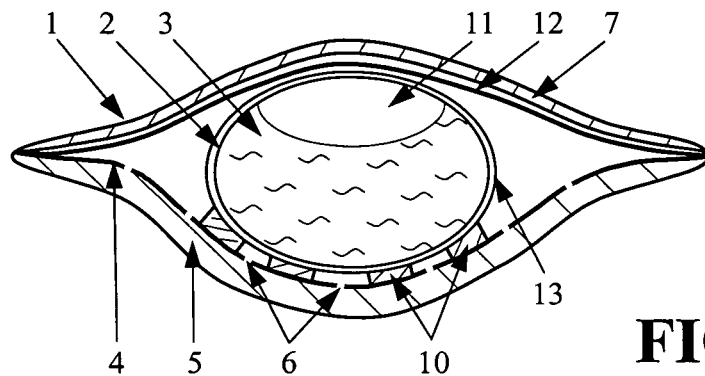
Figure 7B:
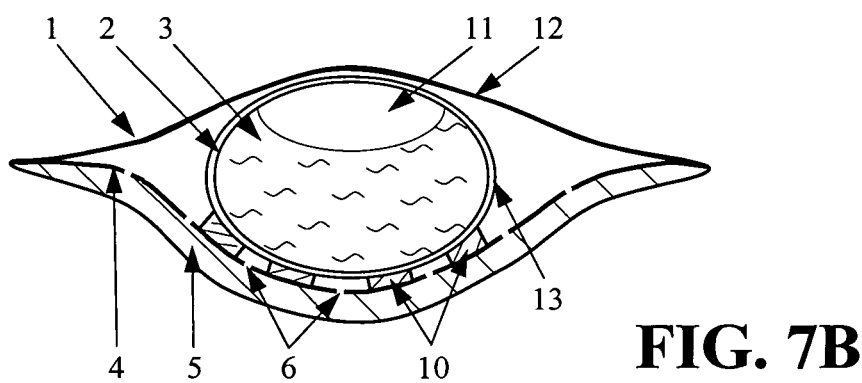
Figure 8:
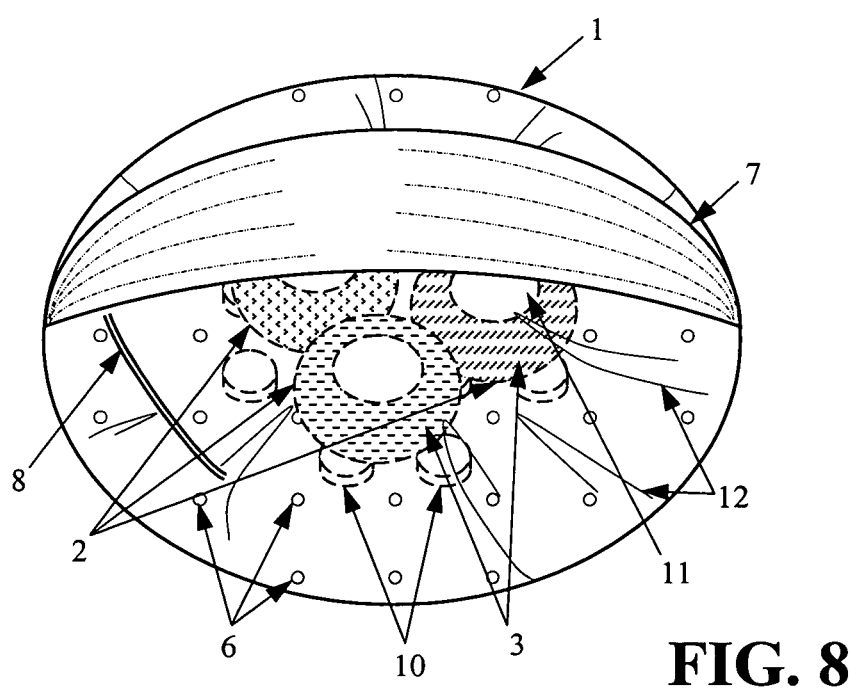
FIG. 8 is a top perspective view of the applicator of this invention containing a plurality of capsules in the storage state.

FIGS. 6A, 6B, 7A, 7B reproduce another implementation of this invention. This is a round, about 5 cm in diameter, applicator 1 that comprises three sheets welded together along their whole edges. The back sheet serves as a transparent impermeable back side 12 of the applicator 1. It is made of an 80-120 micron LDPE film and stretches over the tense spherical capsule 2 (in the top perspective view of FIG. 6A it can be recognized by small radiating folders 12). The user can clearly see the capsule 2 through the back side 12 and press right over the capsule to crash it. A duplication of the back membrane 12 forms a grip 7. An information tab can be inserted into the duplication or a label may be attached to the outside of the grip. The internal sheet of the applicator 1 is a drainable dissector 4 of LDPE comprised of two-three dozens of 0.7 mm equally spaced perforations 6 in an 80-120 micron film and twelve centrally located 1.5 mm thick and 6 mm in diameter discs 10, upon which the capsule 2 rests. The capsule 2 is made of 20 micron LDPE, contains 3.5 ml of a liquid formulation 3 and gas 11 under a positive pressure of 120 mm Hg, and is covered by a nitrocellulose film. Thus, as distinct from the applicator disclosed above, where a capsule is encased in a separate dissector bag composed of perforated and not perforated sides, here the capsule 2 is sandwiched between a perforated bumpy partition (the drainable dissector 4) and the back side 12 of the applicator. (In either embodiments however, the applicator loosely encases the capsule in terms that the volume of the cavity surrounding the capsule considerably exceeds the volume of the capsule itself.) Though, as discussed earlier, the capsule could be fixed by welding to the drainable dissector or to the back side of the applicator, usually it is elastically fixed firmly enough between them to prevent any dislodgment. The front sheet of the applicator is a 3 mm thick fleecy polyester absorber 5 which forms the working side of the applicator (FIG. 7A, 7B).

In the storage position, a 10-15 mm wide flipper-like grip 7 domes over the capsule 2 (FIG. 6A, 7A, 7B). When the user crashes the capsule 2, the released liquid 3 quickly fills the space between the back side 12 of the applicator and the drainable dissector 4 and then streams through channels between disks 10 and perforations 6 to the absorber 5 to evenly infuse it with the liquid. Once the capsule 2 flattens, so does the grip 7, which the user can now easily bring to the upright (working) position and grasp it to apply the liquid formulation (FIG. 6B).

Using fusible materials (thermoplastic material for the drainable dissector and the back side of the applicator; thermoplastic or fibrous material for the absorber) allows simplification of the assembly of the applicator of this embodiment. The absorber, dissector, and the back side of the applicator are essentially hermetically sealed (welded) together along their entire edges in one operation, so that the capsule gets hermetically sealed between the dissector and the back side. Besides, the capsule here is immobilized being elastically compressed between the dissector and the back side of the applicator. The elastic compression is achieved by holding the elastic parts (the dissector or the back membrane or preferably both parts counterbalancing each other) slightly stretched over the capsule until welding is completed. The elastic compression contributes to the positive pressure inside the capsule. Additionally, the same welding operation produces the disclosed grip formed by a duplication of the back membrane. The next step after welding is punching (cutting) a finished applicator along the welding seam.

This embodiment has a number of advantages. Complementing the dissector by the drain is essential for achieving an even distribution of the released liquid. The transparent impermeable back membrane with an attached grip provides with enhanced hygiene and safety of use (no contact of the user's hand with the liquid) and with a visibility of the capsule inside.

As a person skilled in the art would expect, other materials can be used to build an applicator of the same or about the same design. The back side may be made of another suitable material given it is transparent, impermeable for the released liquid, and strong enough to withstand the head of the fluid from a bursting capsule. One should however keep in mind that the back membrane or the dissector or both must be sufficiently rigid to provide the applicator with warp-resistance in use. Otherwise, an additional element of rigidity to support the applicator may be needed.

Figure 9:
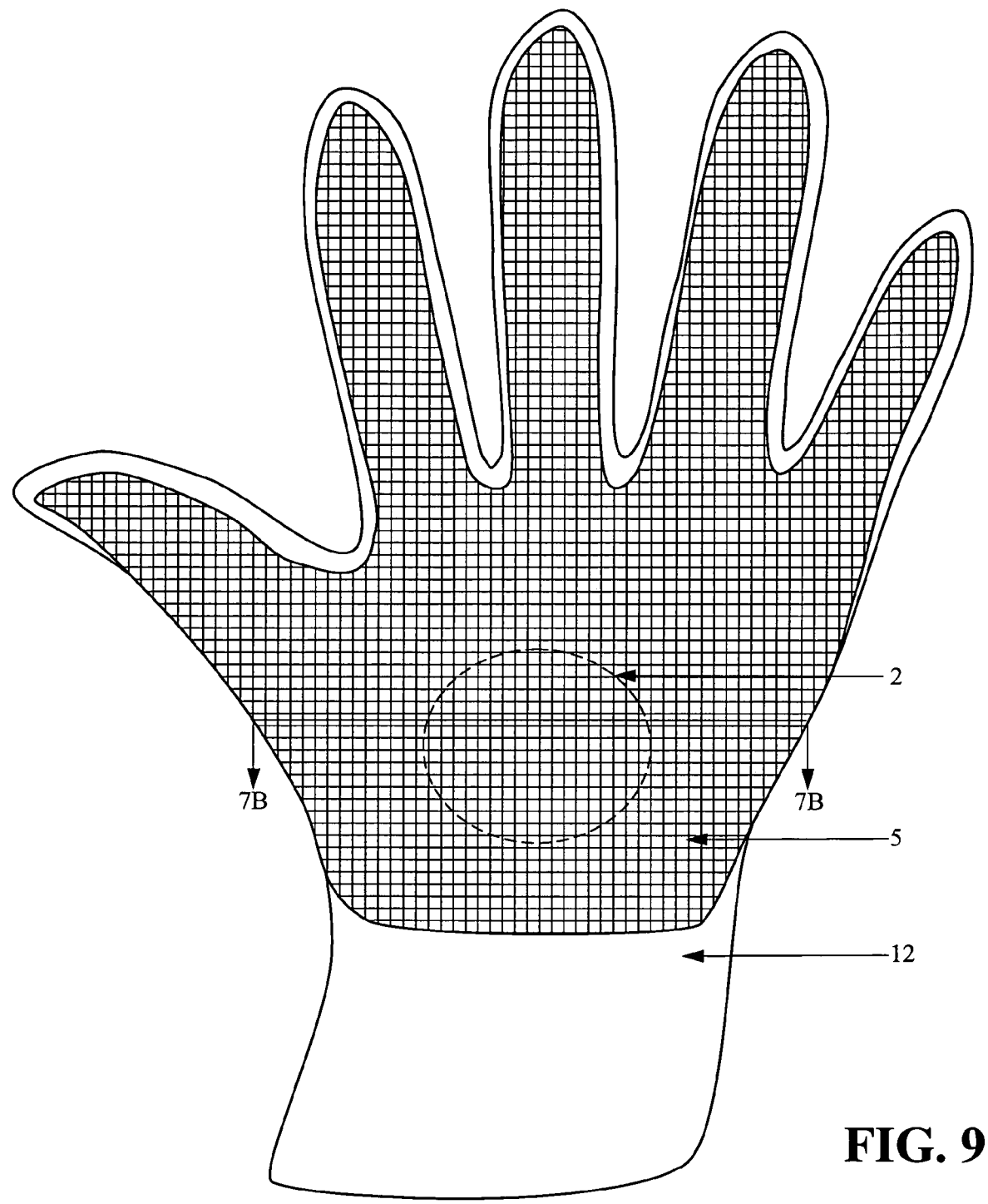
FIG. 9 is a top plan view of the palm of the glove-applicator of this invention.

The use of the disclosed applicator may extend beyond the areas indicated for it as primary (cosmetics, personal care, and medicine). FIG. 9 is a top plan view of the palm of the glove-applicator of this invention. This applicator includes a glove 12 that is impervious for hazardous (i.e. those whose contact with the skin is undesirable) substances of the encapsulated liquid, as it is made of chemically resistant rubber or plastic. The capsule 2, the contour of which is shown by the dashed line, containing a hazardous liquid (such as glue, paint, sealant, solvent, lubricant, cleanser, or repellent) is located between the outside palmar surface of the glove 12 and the spongy absorber 5 lining this surface except for the area occupied by and around the capsule 2. (The palmar surface here includes the area of the palm per se and the palmar surface of fingers.) When the user clenches her hand in the glove-applicator, the capsule 2 ruptures and the liquid infuses the absorber 5. Thus the liquid can be applied on surfaces that can be accessed only or preferably by hand (for example, fine elements of an iron grid that needs painting or a narrow crack in a niche that needs caulking). As in other embodiments, the capsule may be pressurized. The glove-applicator preferably includes the disclosed perforated dissector 4 (FIG. 7B). The capsule must be loosely encased between the glove and the dissector or be loosely encased in a dissector bag. Characteristics of the capsule (pressure at rupture; viscosity of the liquid), dissector (size of perforations), and absorber (porosity; absorbability) should be carefully evaluated and the finished applicator should be thoroughly tested to safeguard against any chance of a hazardous liquid bursting outside when the capsule ruptures. In veterinary, the glove-applicator may be used for applying antiparasitics and other external use medications.

Regarding materials for the disclosed applicator, a person skilled in the art will understand that any material that has not been named in this disclosure (specifically, materials other than LDPE for the capsule; materials other than LDPE or HDPE for the dissector and drain; materials other than polyurethane and polyester for the absorber; materials other than cellulose derivatives for the film coating), but which can provide with additional benefits to the disclosed applicator and its user (such as enhanced convenience for the user, extended storage, enhanced stability of formulations, easier or more accurate dosing, trendier look or more pleasant feel and touch, to mention a few) that are anticipated from its use elsewhere still can be used to build the disclosed applicator.

Although only a limited number of specific embodiments have been described in detail, such description is not to be taken as a limitation of the present invention. The description has been given only as illustration and example. To those skilled in the art, it will be readily apparent that changes may be made without departing from the spirit of the disclosed inventive concepts. The scope of the invention is to be defined by the appended claims.

I claim:

1. A hand applicator of an encapsulated liquid, said applicator including a hand-breakable capsule containing a liquid and an absorber of said liquid, wherein manually squeezing said applicator causes rupture of said capsule and release of said liquid with a subsequent absorption of said liquid by said absorber, said applicator including a perforated dissector of said liquid released hereby, wherein said perforated dissector is placed within the applicator and between said capsule and said absorber, wherein said dissector has a plurality of perforations disposed opposite the entire working surface of said absorber, said plurality of perforations allow an even distribution of the released liquid from said capsule over the entire working surface of said absorber, and a drain for draining the released liquid hereby through said plurality of perforations in said perforated dissector, wherein said drain is formed by a plurality of knobs disposed between said perforated dissector and spaced between said plurality of perforations, said capsule lies on said plurality of knobs and not contacting said perforated dissector and not closing off said plurality of perforations, and wherein channels formed around said plurality of knobs allowing the released liquid from said capsule to freely flow to reach substantially all of said plurality of perforations and subsequently the entire working surface of said absorber.

2. The applicator of claim 1 wherein said drain and said dissector are made as a single element.

3. The applicator of claim 1 wherein said dissector has evenly spaced perforations.

4. The applicator of claim 1 wherein said dissector has perforations only opposite the working side of said applicator.

5. The applicator of claim 1 wherein the total area of perforations in said dissector is less than 10% of the area of said dissector.

6. The applicator of claim 1 wherein said capsule is loosely encased in said applicator.

7. The applicator of claim 1 wherein said capsule is operable to rupture when, upon squeezing hereby, the positive pressure inside said capsule reaches no less than 40 mm Hg.

8. The applicator of claim 1 wherein said capsule contains said liquid under a positive pressure of no less than 40 mm Hg.

9. The applicator of claim 1 wherein said capsule has an impermeable and inert film coating.

10. The applicator of claim 1 wherein said capsule is partially filled with inert gas.

11. The applicator of claim 1 wherein said absorber is operable to fully absorb said liquid released from perforations in said dissector.

12. The applicator of claim 1 including a grip for holding said applicator in hand during application wherein said grip is operable to be brought in the working position only after said capsule ruptures hereby and flattens.

13. The applicator of claim 1 including a fastener for reopening said applicator to refill said applicator with a new said capsule.

14. The applicator of claim 1 wherein said capsule is permanently fixed to said dissector.

15. The applicator of claim 1 wherein said capsule is elastically fixed between said dissector and the back side of said applicator and wherein said dissector and said back side are sealed together along their edges.

16. The applicator of claim 1 including a transparent impermeable back side wherein said capsule is placed between said back side and said dissector.

17. The applicator of claim 1 being a glove that is impervious to said liquid, wherein said absorber covers the outside palmar surface of said glove and wherein said capsule is placed between said surface and said absorber.

* * * * *